United States Patent [19]

Wu

[11] 4,230,885
[45] Oct. 28, 1980

[54] CONVERSION OF AROMATIC CARBOXYLATES TO TEREPHTHALATE

[75] Inventor: Yulin Wu, Bartlesville, Okla.

[73] Assignee: Phillips Petroleum Company, Bartlesville, Okla.

[21] Appl. No.: 914,835

[22] Filed: Jun. 12, 1978

[51] Int. Cl.$^3$ .................. C07C 51/347; C07C 51/353
[52] U.S. Cl. ..................................... 562/481; 562/482
[58] Field of Search ................................ 562/481, 482

[56] References Cited

U.S. PATENT DOCUMENTS

| | | | |
|---|---|---|---|
| 3,093,683 | 6/1963 | Raecke et al. | 562/481 |
| 3,096,366 | 7/1963 | Smith et al. | 562/481 |
| 3,101,368 | 8/1963 | Schenk | 562/481 |
| 3,225,088 | 12/1965 | Takagi et al. | 562/481 |
| 3,641,130 | 2/1972 | Kuper | 562/481 |
| 3,761,515 | 9/1973 | Lind et al. | 562/481 |

Primary Examiner—Jane S. Myers

[57] ABSTRACT

Mixture of salts of aromatic mono- or polycarboxylic acids are converted to terephthalate salts in presence of selected catalyst or catalyst mixture, e.g., a mixture of potassium, sodium and cesium benzoates, is disproportionated in the presence of zinc and/or a zinc salt or a mixture of zinc and/or cadmium and a zinc and/or cadmium salt. The mixture of compounds which are to be converted to terephthalate salts will contain at least those of two different alkali metals. A formula m+n is equal to at least 4 is given for determining the catalyst, or catalysts, to be employed. In one embodiment, now preferred, a mixture of sodium, potassium, and cesium benzoates is heated at a reaction temperature of the order of 350°–430° C., more preferably 380°–415° C., in presence of a catalytic mixture of zinc and cadmium benzoates to obtain high yields and rates of reaction at temperatures substantially below those needed in the prior art for similar or better yields, etc. Other compounds to be converted, catalysts and embodiments are disclosed.

2 Claims, No Drawings

CONVERSION OF AROMATIC CARBOXYLATES TO TEREPHTHALATE

This invention relates to the conversion or disproportionation of metal salts of aromatic mono- or polycarboxylic acids to form terephthalate salts.

In one of its aspects the invention relates to the disproportionation of alkali metal salts of aromatic mono- or polycarboxylic acids in the presence of certain selected catalyst or catalysts.

In one of its concepts the invention provides a process for converting to terephthalate salts a mixture of at least two different compounds, i.e. compounds of at least two different alkali metals selected from potassium, sodium and cesium, disclosed herein, in the presence of a catalyst herein defined, rendering possible an economically feasible operation, including the savings of large amounts of energy, which can be conducted at temperatures lower than those usually needed yet to obtain high conversion or yield and concomitant high reaction rates, the process comprising the conversion of a mixture of metal salts of aromatic mono- or polycarboxylic acids in which the metal is selected from alkali metals and group IIA metals, the reaction is effected in presence of at least one catalytically active metal or compound of a metal selected from groups IB, IIB, IIIB, IVB, VB, VIB, VIIB and VIII of the periodic table of elements (derived from "Kirk-Othmer Encyclopedia of Chemical Technology," Vol. 8, 2nd Ed., John Wiley & Sons, Inc., New York, 1965, p. 94) and lead, including metal-organic and complex compounds thereof, wherein m is an integer equal to at least 2 and represents the number of said different alkali metals in the mixture of compounds being converted, n is an integer equal to at least 1 and represents the number of catalytic species present during the conversion, m+n is an integer which must be equal to at least 4, when n equals 1 the catalytic material is selected from group IIB metal and salts, when n equals at least 2 the catalytic materials are at least 2 metals or salts selected from groups IB, IIB, IIIB, IVB, VB, VIB, VIIB, VIII and lead.

In the disproportionation of alkali metal benzoates to terephthalate salts and benzene in the presence of a zinc benzoate catalyst, a reaction temperature of around 450° C. is normally required to obtain commercially attractive reaction rates and yields. These temperatures can cause some thermal decomposition of dispersant and reactants, a buildup of decomposition products in transfer lines, and excessive energy consumption. A process wherein the disproportionation reaction could be conducted at lower temperatures with reaction rates and product yields comparable with or better than those at 450° C. without being economically prohibitive would be a significant improvement.

The process of this invention provides an economically attractive method of disproportionation of benzoate salts to terephthalate salts and benzene at reaction temperatures of around 400° C. with high reaction rates and high yields.

U.S. Pat. Nos. 3,093,683 issued June 11, 1963; 3,096,366 issued July 2, 1963; 3,641,130 issued Feb. 8, 1972 and 3,873,609 issued Mar. 25, 1975 variously relate to and disclose information concerning the transformation of aromatic polycarboxylic acids and their salts to terephthalic acids, etc. Their disclosures are incorporated herein by reference.

As a result of extensive work and analysis, I have discovered that certain metal salts of aromatic mono- or polycarboxylic acids can be converted to terephthalate salts and benzene at temperatures substantially lower than those heretofore thought necessary and employed albeit without giving up, indeed obtaining, high reaction rates and high yields. Much energy is saved in my process which can be operated at substantially lower temperatures and therefore lower cost on heat input and heat loss during operation.

More specifically, I have discovered certain combinations of compounds to be converted in the presence of catalysts, as herein defined, to effectively produce terephthalate salts at relatively low cost.

The compounds converted and the catalysts used are known in the art. My invention deals with certain combinations of the known compounds and known catalysts which combinations have been found surprisingly to permit high reaction rates and high yields even though operation is generally at considerably lower temperatures with concomitant heat savings.

An object of this invention is to provide an improved process for the catalytic formation of terephthalate salts. Another object of the invention is to provide a process for the formation of alkali metal salts of aromatic polycarboxylic acids. A further object is to provide an improved catalytic disproportionation system for formation of salts of polycarboxylic acid. A further object of the invention is to provide combinations of compounds and catalysts permitting economically feasible operation with concomitant heat savings, yet without sacrificing high yield and high reaction rates. Other aspects, concepts, objects and the several advantages of this invention are apparent from this disclosure and the appended claims.

According to the present invention there is provided a process for converting to terephthalate salts a mixture of at least two different compounds having the formula

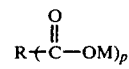

wherein R is selected from aromatic and alkyl aromatic groups having 6 to about 30 carbon atoms, M is selected from alkali metals and group IIA metals and p is the integer 1, 2, 3, 4, 5, or 6 which comprises heating said mixture to a reaction temperature in the presence of at least one catalytically active metal or compound of a metal selected from groups IB, IIB, IIIB, IVB, VB, VIB, VIIB and VIII of the periodic table of the elements and lead, including metal-organic and complex compounds thereof, wherein m is an integer equal to at least two and represents the number of different alkali metals in the mixture of compounds being converted, n is an integer equal to at least 1 and represents the number of catalytic species present during the conversion, m+n is an integer which must equal at least 4, when n equals 1 the catalytic material is selected from group IIB metal and salts, when n equals at least 2 the catalytic material is at least 2 metals or salts selected from groups IB, IIB, IIIB, IVB, VB, VIB, VIIB, VIII and lead.

Still according to the invention, in one embodiment thereof, there are converted mixtures of alkali metals salts of aromatic mono- or polycarboxylic acids containing at least 2 different alkali metal carboxylates which are included in the above-given formula in the presence of a catalyst or catalyst system also included in the above description.

Still according to the invention the temperature of operation of the process defined herein can be conducted economically yet with high reaction rates and yields at a temperature in the approximate range of from about 350° to about 430° C., preferably at a temperature of reaction of the order of from about 380° to about 415° C.

The alkali metals include lithium, sodium, potassium, rubidium, and cesium. Group IIA metals beryllium, magnesium, calcium, strontium, and barium are also suitable for use as salts of the mono- or polycarboxylic acids.

Such salts are readily prepared from the corresponding acids. Such acids include, for example, benzoic acid, 2-napthalenecarboxylic acid, 4-biphenylcarboxylic acid, 2,6-naphthalenedicarboxylic acid, phthalic acid, isophthalic acid, terephthalic acid, 2-anthracenecarboxylic acid, 1,5-anthracenedicarboxylic acid, 1,5,9-anthracenetricarboxylic acid, 2,4,6-trimethylbenzene-1,3-dicarboxylic acid, 2-ethyl-4-hexyl-6-methylbenzene-1,3-dicarboxylic acid, 2,4-dibutylbenzene-1,3,5-tricarboxylic acid, and the like.

In all the above-mentioned carboxylic acid salts the aromatic ring may carry alkyl radicals, in addition to the carboxylate groups, provided that these alkyl radical substituents do not bring about a decomposition of the molecule at temperatures equal to or lower than the reaction temperature.

For reasons of availability and cost as well as for value of the disproportionation product, benzoic acid is the currently preferred carboxylic acid for use in the process of this invention.

The currently preferred carboxylic acid salts for the practice of this invention are the alkali metal benzoates. For reasons of reactivity, the more preferred benzoate salt mixtures contain potassium benzoate and one or more other alkali metal benzoates. For reasons of reactivity and cost, the currently most preferred benzoate salt mixtures contain potassium, sodium and cesium benzoates.

The amount of each alkali metal aromatic carboxylate utilized in the practice of this invention for $m=2$ will generally be greater than about 2 weight % of the total alkali metal aromatic carboxylates mixture. When potassium is utilized as one of the alkali metals, the amount of potassium carboxylate will preferably be from about 10 to about 98 weight % and the amount of the second alkali metal carboxylate will preferably be from about 90 to about 2 weight %, with each percentage based on the total weight of alkali metal carboxylates charged to the reactor.

The amount of each alkali metal aromatic carboxylate utilized in the practice of this invention for $m=3$ or more will generally be about 2 weight % or more of the total alkali metal aromatic carboxylates weight. When potassium is utilized as one of the alkali metals, the amount of potassium carboxylate will preferably be from about 40 to about 85 weight % and the amount of each of the other alkali metal carboxylates will be about 2 weight % or greater of the total alkali metal aromatic carboxylates. When the currently most preferred mixtures containing sodium, potassium, and cesium benzoates are utilized, they will contain from about 10 to about 55 weight % sodium benzoate, from about 40 to about 85 weight % potassium benzoate, and from about 2 to about 20 weight % cesium benzoate, based on the total weight of the alkali metal carboxylates mixture.

The reaction products obtained by operation of the process of the present invention are alkali metal salts of dicarboxylic acids which are readily convertable to corresponding dicarboxylic acids.

The catalysts utilized in the catalyst system of this invention are metals selected from groups IB, IIB, IIIB, IVB, VB, VIB, VIIB, and VIII of the periodic table of the elements and lead as well as catalytically active compounds of these metals such as salts formed with inorganic or organic acids and their metal-organic or their complex compounds, among others, their carbonates, bicarbonates, halides, sulfates, formates, phosphates, oxalates, fatty acid salts or the salts of the above metals formed with those acids which may serve as starting materials for the reaction according to the invention or which are formed by this reaction, for example, their benzoates, phthalates or terephthalates, or precursors of these salts such as mixtures of metal oxides and aromatic carboxylic acids.

Examples of catalytic materials suitable for use in the catalyst system of this invention include the free metals and salts of copper, silver, gold, zinc, cadmium, mercury, lanthanum, cerium, thorium, zirconium, vanadium, manganese, iron, cobalt, nickel, tungsten, lead, and the like. Examples of specific metal salts and salt precursors include zinc benzoate, cadmium benzoate, silver benzoate, iron benzoate, mixtures of zinc oxide and benzoic acid, mixtures of cadmium oxide and benzoic acid, and the like. When mentioned below, the term "salts" is intended to also include salt precursors.

The number of catalytic species utilized in this invention is n wherein n is an integer equal to 1 or more and wherein the total $m+n$ is an integer equal to 4 or more. When $n=1$, the catalytic material is selected from the group IIB metals and their salts, including zinc, cadmium, and mercury and their salts. For economic reasons, zinc or zinc salts are the preferred catalytic material when $n=1$. Cadmium, because of cost, is not now preferred. When $n=2$ or more, the catalytic materials are two or more metals selected from groups IB, IIB, IIIB, IVB, VB, VIB, VIIB, VIII, and lead and their salts. The preferred catalytic materials when $n=2$ or more are zinc or cadmium metals or their salts and one or more metals selected from groups IB, IIB, and VIII and their salts. For reasons of reactivity and availability, the currently most preferred catalytic system when $n=2$ is a mixture of zinc and cadmium salts, such as zinc benzoate and cadmium benzoate.

The total amount of catalyst used can vary within wide limits and can range from 0.1 to 100 grams of catalyst per mole of aromatic carboxylate employed, more preferably in the range of 1 to 50 grams per mole. The catalysts can be especially finely divided throughout the reaction mixture by transforming an aqueous solution of the alkali metal salts serving as the starting materials, which contain the catalysts dissolved or suspended therein, into a dry powder by spray-drying or by other suitable methods.

When two catalytic materials are used ($n=2$), any ratio of the two components can be used, although preferably each component will be present in amounts greater than about 10 mole % of the total catalyst. When three or more catalytic materials are used ($n=3$ or more), any ratio of the three components can be used, although preferably each component will be present in amounts greater than about 5 mole % of the total catalyst.

In a currently preferred embodiment of this invention, a mixture of sodium benzoate, potassium benzoate, and cesium benzoate is disproportionated in the presence of zinc benzoate and cadmium benzoate to terephthalate salts which are readily converted to terephthalic acid.

In a now preferred embodiment of the invention there is employed a dispersant, e.g., an organic adjuvant dispersant.

Organic dispersants useful herein are those which will not appreciably decompose under the conditions of the process, and are substantially inert to the reactants, and are relatively high-boiling. Such organic dispersants include aromatic hydrocarbons selected from the group consisting of polyaromatic compounds having two or more aromatic rings, polynuclear aromatic compounds and mixtures thereof. Examples of such organic dispersants include biphenyl, terphenyls, quaterphenyls, pentaphenyls and heavier polyphenyls; binaphthyls; naphthalene, anthracene, phenanthrene, pyrene, triphenylene, chrysene, perylene, pentacenyl, and mixtures thereof.

It is desirable that the organic dispersant remain in the liquid state throughout the process; thus, the compound should have a melting point below about 150° C. Mixtures of two or more of the compounds can be utilized to reduce the melting point of the dispersant. It is also desirable that the dispersant have a relatively high boiling point, for example, above about 250° C., in order to aid in maintaining the reaction pressure at a low level.

The organic dispersant is present in the slurry in an amount in the range of from 25 to 80 percent by weight of the total weight of the slurry and preferably in an amount in the range of from 60 to 75 percent by weight of the total weight of the slurry.

The slurry is formed by mixing the organic dispersant with the alkali metal salts of the aromatic carboxylic acid desired to be transformed. Any conventional method of mixing a solid with a liquid can be used to form the slurry. For example, if a batch reactor is employed, the dispersant, in liquid form, is added to the reactor; then the solid salts to be converted, such as potassium benzoate, and sodium benzoate, and suitable disproportionation catalysts, such as zinc benzoate and cadmium benzoate, all preferably in finely divided form, are added to the reactor while the liquid is being stirred. If a continuous reactor is employed, the solids are metered into a separate stirred mix tank which contains the liquid dispersant wherein the slurry is formed, and the slurry is then introduced into the reactor. After mixing, the process proceeds according to the well-known disproportionation process. Thus, the slurry, comprised of an alkali metal salt of an aromatic carboxylic acid and suitable disproportionation catalysts, is subjected to heating in a gas atmosphere in order to effect the conversion of the alkali metal salts to the desired aromatic polycarboxylate.

Even though inert not all dispersants which are organic will yield presently acceptable results. The routineer can determine by routine tests the dispersant optimum for his purposes, whether the dispersant is herein disclosed or not.

The disproportionation reaction of this invention can also be conducted without a dispersant. Thus, the reactants are caused to be molten in the presence of the catalyst in the absence of a dispersant.

The conversion of the alkali metal carboxylates is effected substantially completely in the absence of oxygen or water.

The process of this invention is carried out in presence of carbon dioxide and other inert gas atmospheres. Examples of such gases include nitrogen, methane, argon, neon, butane, ethane, helium and the like. When carbon dioxide is employed, the atmosphere will preferably contain at least 50 mol percent carbon dioxide. However, the presence of carbon dioxide or other gases specifically named is not essential to obtain the high conversion of initial reactant in the atmosphere in which the thermal conversion is carried out. In addition, carbon monoxide or a mixture of CO and $CO_2$ can be used in carrying out the process of the invention.

Pressures in the range of 0 to 5000 psig or more can be employed, but it is advantageous and preferable, in keeping with one embodiment of the invention, that lower pressures in the range of 0 to 1000 psig be employed.

Sufficient reaction time should be employed to effect the desired degree of conversion. Generally, reaction times in the range of about 1 second to about 48 hours, preferably 5 seconds to 2 hours, are suitable.

The temperature utilized in the practice of the process of this invention will be broadly in the range from about 350° to about 430° C., preferably from about 380° to about 415° C.

The aromatic polycarboxylates which are produced according to the process of this invention can be recovered from the reaction effluent slurry by extraction with an aromatic solvent such as benzene, toluene, and the like or by an evaporation method whereby the inert organic dispersant is separated from the reaction product by evaporation or sublimation while the reaction products are hot, i.e., 300° C. to 440° C. In addition, the aromatic polycarboxylates can be recovered from the reaction effluent slurry by adding water to the slurry followed by agitation and settling. The water, being substantially completely immiscible with the organic dispersant, separates as a separate liquid phase carrying with it in solution the water-soluble aromatic polycarboxylates. The organic dispersant phase which contains the catalyst residue is easily removed from the water phase by conventional phase separation techniques, such as by decantation.

In addition, the specific disproportionation reaction of this invention, generally can be conducted and the product recovered by a process as described in earlier-mentioned U.S. Pat. No. 3,873,609.

Unless otherwise stated, the runs described in the following examples were carried out in a 30 ml #316 stainless steel reactor which was fitted with a pressure gauge, thermocouple, and inlet tube for pressuring the reactor with $CO_2$. The reactor was heated in an electrically heated Wood's alloy bath.

The alkali metal benzoates were prepared by neutralizing benzoic acid (Eastman Kodak Co., analytical grade) with the appropriate alkali metal hydroxide [NaOH, KOH, or CsOH (Research Organic-Inorganic Chemical Corp., 99.9% purity)]. Water was evaporated until solid was present and the mixture was cooled and filtered. The alkali metal benzoate was dried in an oven at 110° C. overnight.

The zinc, cadmium, silver, and iron benzoate catalysts were prepared by mixing zinc chloride, cadmium chloride, silver nitrate, or ferric chloride with potassium benzoate in water at 60°–70° C. The resulting metal benzoate was filtered and oven dried overnight at 110°–120° C.

The terphenyl used in the runs was from Rhone-Poulenc Industries and contained 75.3 weight % m-terphenyl, 19.9 weight % O-terphenyl, and 4.4 weight % p-terphenyl.

Unless otherwise stated, each run in the following examples was conducted using the following "standard" procedure. The desired amount of alkali metal benzoate(s) and metal benzoate catalyst(s) were mixed using mortar and pestle and then mixed with terphenyl (a 2/1 weight ratio of terphenyl to total alkali metal benzoate was used). The mixtures were charged to the reactor and the reactor was sealed, purged with carbon dioxide three times, and pressured to about 250 psig (1.72 MPa) with $CO_2$. The reactor was dropped into a preheated Wood's alloy bath and the reaction was carried out for the desired length of time at the desired temperature. During the reaction, pressure in the reactor was between about 600 and about 800 psig (4.14 to 5.5 MPa).

At the conclusion of the reaction period, the reactor was removed from the heating bath and was quenched in chilled water. The reactor was vented and opened and the contents were removed. The reaction mixture was mixed with benzene or toluene. The solid, which normally contained about 85 weight % terephthalic acid (TPA), about 7 weight % phthalic acid, and about 0.3 weight % isophthalic acid, was oven dried at 110°–120° C. overnight and mixed with distilled water. The water-insoluble material was filtered from the alkali metal salt solution and the solution was acidified with 6 N HCl. The resulting mixture was heated to about 95° C. and filtered and the residue was washed with hot water. The residue, which normally contained about 98 mole % TPA, was oven dried at 110° C. for 2 hours and was weighed. Since the disproportionation reaction involves the conversion of the alkali metal benzoates to TPA salts and benzene, TPA yields were calculated based on the amount of alkali metal benzoate charged to the reactor according to the equation:

$$TPA\ Yield\ (\%) = \frac{\text{Moles of diacid recovered}}{\frac{1}{2} \times \text{Moles of alkali metal benzoate charged}} \times 100$$

In some runs, the crude TPA product was esterified by mixing it with 50 ml methanol and 0.4 ml of concentrated sulfuric acid. The resulting dimethyl-esters were analyzed by gas chromatography to confirm the TPA yield and to determine the isomer ratios.

In some runs, the reaction products were analyzed by liquid chromatography to determine their components, especially, mono- and dicarboxylate isomers.

The following abbreviations are used in the examples:
NaBz = sodium benzoate
KBz = potassium benzoate
CsBz = cesium benzoate
$ZnBz_2$ = zinc benzoate
$CdBz_2$ = cadmium benzoate
AgBz = silver benzoate
$FeBz_3$ = iron benzoate (ferric benzoate)
TPA = terephthalic acid EXAMPLE I—Single Benzoate, Single Catalyst A series of runs was carried out using a single alkali metal benzoate and zinc benzoate as a catalyst. The quantities of the materials used, the reaction conditions, and the TPA yields are shown in Table I.

TABLE I

| Run No. | Alkali Metal Benzoate (g) | $ZnBz_2$ g | Reaction Temp., °C. | Reaction Time Hr. | TPA Yield mole % |
|---|---|---|---|---|---|
| 1 | NaBz (2) | 0.1 | 440 | 2 | trace |
| 2[a] | KBz (1) | 0.1 | 360 | 2 | trace |
| 3 | KBz (2) | 0.14 | 390 | 2 | trace |
| 4[a] | KBz (1) | 0.05 | 404 | 2 | trace |
| 5 | KBz (3) | 0.3 | 440 | 2 | 74 |
| 6 | CsBz (2) | 0.1 | 303 | 2 | trace |
| 7 | CsBz (2.1) | 0.11 | 364 | 2 | 80 |
| 8 | CsBz (2) | 0.1 | 391 | 2 | 88 |

[a]Reactor charge included 1 g. of magnesium benzoate.

The results of these runs show that a combination of one alkali metal benzoate (m=1) and one metal benzoate catalyst (n=1), which is outside the scope of this invention, i.e., m+n=2, produced good TPA yields at reaction temperatures of about 400° or below only with economically prohibitive cesium benzoate, sodium benzoate (run 1) was ineffective even at 440° C. Potassium benzoate was ineffective at reaction temperatures between 360° and 404° C. (runs 2 and 4) with or without added magnesium benzoate and was effective at 440° C. (run 5). Run 5 is believed to represent a typical prior art disproportionation reaction. Cesium benzoate, an expensive material which would not be economically feasible in a commercial plant, was ineffective at 303° C. (run 6), but was effective at 364° and 391° C. (runs 7 and 8).

EXAMPLE II—Two Benzoates—Single Catalyst

A series of runs was carried out utilizing mixtures of two alkali metal benzoates and with zinc benzoate as a catalyst. The quantities used, reaction conditions, and TPA yields for each run are summarized in Table II.

TABLE II

| Run No. | NaBz, g | KBz, g | CsBz, g | $ZnBz_2$, g | Reaction Temp., °C. | Reaction Time, Hr. | TPA Yield, mole % |
|---|---|---|---|---|---|---|---|
| 9 | 1.44 | 1.6 | — | 0.12 | 390 | 2 | 36 |
| 10 | 1.44 | 1.6 | — | 0.06 | 400 | 2 | 39 |
| 11 | 1.44 | 1.6 | — | 0.3 | 404 | 2 | 15 |
| 12 | — | 1 | 1 | 0.1 | 400 | 2 | 89 |
| 13 | — | 2 | 0.1 | 0.1 | 400 | 2 | trace |
| 14 | 2 | — | 0.1 | 0.1 | 404 | 2 | trace |

The results of these runs, which are not according to the invention, as defined, with m=2 and n=1, for a total m+n=3, show increases in TPA yield at reaction temperatures near 400° C. compared with runs in Table I. A high TPA yield was obtained at 400° C. with equal weights of potassium and cesium benzoate (run 12). However, disproportionation reactions using this much of the expensive cesium benzoate are not commercially feasible while reactions with lower levels of cesium benzoate are ineffective (runs 13 and 14). Runs using mixtures of sodium and potassium benzoates (runs 9 to 11) have TPA yields above the yields obtained using sodium or potassium benzoates alone (runs 1 and 3), but these yields are not commercially attractive.

EXAMPLE III—Three Benzoates, Single Catalyst

A series of runs was carried out using three alkali metal benzoates and with zinc benzoate as a catalyst.

The quantities of materials, reaction conditions, and TPA yields for each run are summarized in Table III. Runs according to the claimed invention are included. See Runs 15-20, inclusive.

TABLE III

| Run No. | NaBz, g | KBz, g | CsBz, g | ZnBz$_2$, g | Reaction Temp., °C. | Reaction Time, Hr. | TPA Yield mole % |
|---|---|---|---|---|---|---|---|
| 15 | 1.44 | 1.6 | 0.12 | 0.12 | 372 | 2 | 24 |
| 16 | 1.44 | 1.6 | 0.12 | 0.12 | 380 | 2 | 68 |
| 17 | 1.44 | 1.6 | 1.12 | 1.12 | 390 | 2 | 77 |
| 18 | 1.44 | 1.6 | 0.12 | 0.12 | 401 | 2 | 78 |
| 19 | 1.44 | 1.6 | 0.06 | 0.12 | 400 | 2 | 71 |
| 20 | 1.44 | 1.6 | 0.06 | 0.09 | 400 | 2 | 67 |
| 21 | 1.44 | 1.6 | 0.03 | 0.06 | 400 | 2 | 41 |
| 22[a] | 1.44 | 1.6 | 0.12 | 0.12 | 380 | 2 | 38 |
| 23 | 1.44 | 1.6 | 0.12 | 0.12 | 420 | 1 | 70 |
| 24 | 1.44 | 1.6 | — | 0.12 | 420 | 1 | 64 |
| 25 | 1.40 | 1.6 | 0.12 | — | 390 | 2 | trace |
| 26[b] | 1.44 | 1.6 | 0.12 | 0.12 | 404 | 1 | 38 |
| 27[c] | 1.44 | 1.6 | 0.12 | 0.12 | 402 | 1 | 46 |
| 28[d] | 1.44 | 1.6 | 0.12 | 0.12 | 405 | 1 | 70 |

[a] The reaction dispersant was hexadecane.
[b] Final reactor pressure = 375 psig.
[c] Final reactor pressure = 515 psig.
[d] Final reactor pressure = 625 psig.

The results of runs 15 through 20, which are according to the invention, with m=3 and n=1 for a total of m+n=4, show that good TPA yields are obtained at reaction temperatures around 400° C. and appreciable amounts of TPA are formed at reaction temperatures as low as 372° C. This is in sharp contrast with runs 9 to 11 in Table II, without cesium benzoate, and run 13 without sodium benzoate in which runs the TPA's were 36, 39, 15 and trace, respectively.

The high TPA yields of the instant invention are seen in runs 18 to 21 to decrease at the lowest cesium benzoate levels (about 1 weight % cesium benzoate based on the total weight of alkali metal benzoates). Therefore, the presence and amount of cesium benzoate are important factors in the successful utilization of this invention with a single catalyst. The ZnBz$_2$ catalyst level was also decreased in runs 20 and 21. However, a comparison of run 21 with run 10 shows that the presence of 1% cesium benzoate at the same ZnBz$_2$ catalyst level provides little change in TPA yield.

Run 22 was conducted in a hexadecane dispersant, not now preferred, because a TPA yield significantly below that of run 16, which was conducted in terphenyl, was obtained. The hexadecane may have reacted.

The results of runs 23 and 24 indicate that the advantage of the presence of cesium benzoate is less at 420° C. than at about 400° C.

Run 25 at 390° C. in the absence of the ZnBz$_2$ catalyst shows that only a trace amount of TPA is formed and this TPA is probably formed by the well-known thermal disproportionation reaction.

Run 25 demonstrates that cesium benzoate was not catalytic when used alone with sodium and potassium benzoates at 390° C. Runs 12 and 13, Table II show the use of substantially more than a catalytic amount of cesium benzoate was needed to obtain a high yield. The pressure developed during the disproportionation reaction, which is determined by the CO$_2$ pressure applied to the reaction at the start of the run, is shown in runs 26 to 28 to have a significant influence on TPA yield with higher pressures yielding higher TPA yields.

The results of the runs of this example demonstrate the value of the instant invention for the preparation of TPA in good yield at temperatures around 400° C. from mixed alkali metal benzoates containing low levels of the expensive cesium benzoate.

EXAMPLE IV

A series of runs was carried out using three alkali metal benzoates and zinc benzoate as catalyst to demonstrate the effect of the levels and ratios of the reaction components on TPA yields. The previously described procedure was used. The quantities of materials, reaction conditions, and TPA yields in each run are summarized in Table IV. Run 14 is included in the table for comparison.

TABLE IV

| Run No. | NaBz, g | KBz, g | CsBz, g | ZnBz$_2$, g | Reaction Temp., °C. | Reaction Time, Hr. | TPA Yield, mole % |
|---|---|---|---|---|---|---|---|
| 29 | — | 3.2 | 0.12 | 0.12 | 406 | 1 | 23 |
| 30 | 0.288 | 2.88 | 0.12 | 0.12 | 406 | 1 | 24 |
| 31 | 0.72 | 2.4 | 0.12 | 0.12 | 407 | 1 | 60 |
| 32 | 0.96 | 2.13 | 0.12 | 0.12 | 403 | 1 | 61 |
| 33 | 1.15 | 1.92 | 0.12 | 0.12 | 405 | 1 | 58 |
| 34 | 1.44 | 1.60 | 0.12 | 0.12 | 407 | 1 | 55 |
| 35 | 1.92 | 1.07 | 0.12 | 0.12 | 407 | 1 | 32 |
| 36 | 2.3 | 0.64 | 0.12 | 0.12 | 403 | 1 | 27 |
| 14 | 2 | — | 0.1 | 0.1 | 404 | 2 | trace |
| 37 | 0.96 | 2.13 | 0.24 | 0.12 | 406 | 1 | 66 |
| 38 | 0.96 | 2.13 | 0.12 | 0.24 | 405 | 1 | 65 |

The results of these runs show the critical nature of the sodium benzoate and potassium benzoate levels in the disproportionation reaction of this invention. Low TPA yields were obtained at sodium benzoate levels below about 10 weight % based on the total weight percent of alkali metal benzoates (runs 29 and 30). Low TPA yields were obtained at potassium benzoate levels below about 40 weight % based on the total weight of alkali metal benzoates (runs 35, 36 and 14). Cesium benzoate levels below about 2 weight % based on the total weight of alkali metal benzoates also result in a low TPA yield (run 21 of Table III). Higher levels of cesium benzoate (run 37) or zinc benzoate (run 38) result in a slight increase in TPA yield compared with run 32.

EXAMPLE V

A series of runs was carried out using combinations of zinc benzoate and cadmium benzoate to catalyze the disproportionation mixtures of alkali metal benzoates to TPA. The previously described procedure was used. The amounts of materials, reaction conditions, and TPA yields in each run are presented in Table V. Runs 9 and 29 are included in the table as control runs.

TABLE V

| Run[a] No. | NaBz, g | KBz, g | CsBz, g | ZnBz$_2$, g | CdBz$_2$, g | Temp. °C. | TPA Yield, mole % |
|---|---|---|---|---|---|---|---|
| 39 | 1.0 | — | 1.0 | 0.1 | — | 378 | trace |
| 40 | 1.0 | — | 1.0 | — | 0.1 | 378 | 44 |
| 41 | 2.88 | — | — | — | 0.12 | 408 | trace |
| 42 | — | 3.2 | — | — | 0.12 | 406 | 62 |
| 43 | 1.44 | 1.6 | — | — | 0.06 | 408 | 66 |
| 44 | 1.44 | 1.6 | — | — | 0.12 | 407 | 79 |
| 9 | 1.44 | 1.6 | — | 0.12 | — | 390 | 36 |
| 29 | — | 3.2 | 0.12 | 0.12 | — | 406 | 23 |
| 45 | — | 3.2 | 0.12 | 0.06 | 0.06 | 407 | 77 |
| 46 | 1.44 | 1.60 | — | 0.06 | 0.06 | 402 | 84 |
| 47[b] | 1.44 | 1.60 | — | 0.06 | 0.06 | 408 | 87 |
| 48 | 1.44 | 1.60 | — | 0.06 | 0.06 | 378 | 42 |
| 49[c] | 1.44 | 1.60 | — | 0.06 | 0.06 | 403 | 72 |
| 50[d] | 1.44 | 1.60 | — | 0.06 | 0.06 | 408 | 71 |

TABLE V-continued

| Run[a] No. | NaBz, g | KBz, g | CsBz, g | ZnBz₂, g | CdBz₂, g | Temp. °C. | TPA Yield, mole % |
|---|---|---|---|---|---|---|---|
| 51[e] | 8.7 | 19.2 | 1.2 | 0.6 | 0.6 | 405 | 91 |
| 52[e] | 8.7 | 19.2 | 1.2 | 0.6 | 0.6 | 407 | 87 |

[a]All runs were carried out for 1 hour except where noted otherwise.
[b]Reaction time = 2 hours
[c]Reaction pressure = 625–680 psig.
[d]Reaction pressure = 410–480 psig.
[e]A 300 ml S.S. autoclave was used.

Runs 39 to 44, 9, repeated from Table II, and 29, repeated from Table IV, are control runs with $m=1$ or 2 and $n=1$ for a total $m+n=2$ or 3. Cadmium benzoate was found to be more active as a catalyst than the same weight of zinc benzoate. However, cadmium benzoate is so expensive that its use as the sole catalytic agent in a commercial disproportionation process is not now preferred. Runs 45 to 50 are invention runs at reaction temperatures of 378° C. and around 400° C. with $m=2$ and $n=2$ for a total $m+n=4$. Very good TPA yields were obtained using the process of this invention while using much less of the expensive cadmium benzoate catalyst than in runs 40–42 and 44. In run 43 the temperature of 408° C. is to be compared with the temperature of 380° C. of run 16 in Table III. Energy considerations also are involved in selecting preferred catalysts. Surprisingly, the 84% TPA yield in run 46 was higher than in runs using either catalyst separately (run 44, 79%, and run 9, 36%, at 390° C. and run 24, 64%, at 420° C.) at the same weight as the total weight of the two catalysts in run 46. Pressure appears to influence yield of TPA at any given temperature, assuming other parameters constant. Thus, the lower yields in runs 49 and 50 appear to be a result of reaction pressures lower than in, say, run 46 in which the pressure was 800–815 psig. Lower reaction pressures were shown in previous examples (see runs 26, 27, and 28 of Table III) to result in lower TPA yields.

Runs 51 and 52 are invention runs at about 405° C. with $m=3$ and $n=2$ for a total $m+n=5$. Outstanding TPA yields were obtained in these runs, thus demonstrating the currently preferred mode of operation of this invention.

EXAMPLE VI

A series of runs was conducted to demonstrate the use of various combinations of zinc benzoate and cadmium benzoate as catalysts for the disproportionation of a mixture of sodium benzoate, potassium benzoate, and cesium benzoate. The previously described procedure was used. The quantities of materials, reaction conditions, and results in each run are shown in Table VI.

TABLE VI

| Run[a,b] No. | ZnBz₂, ×10⁻⁴ mole | CdBz₂, ×10⁻⁴ mole | ZnBz₂[c], mole % | Reaction Temp. °C. | TPA Yield mole % |
|---|---|---|---|---|---|
| 53 | 3.7 | — | 100 | 403 | 64 |
| 54 | 2.63 | 1.03 | 72 | 401 | 88 |
| 55 | 1.58 | 2.16 | 42 | 403 | 90 |
| 56 | 1.04 | 2.67 | 28 | 399 | 87 |
| 57 | — | 3.67 | 0 | 405 | 81 |

[a]Reaction time = 1 hour
Reaction pressures = 780 to 805 psig.
[b]Alkali metal benzoates:
KBz = 1.98 g.
NaBz = 0.897 g.
CsBz = 0.124 g.
[c]Mole % ZnBz₂ based on the total catalyst content.

The results of these runs show that TPA yields greater than the yields obtained with either catalyst alone were obtained with a combination of the two catalysts containing zinc benzoate at levels from 28 to 72 mole % based on the total catalyst content.

EXAMPLE VII

A series of runs was carried out to demonstrate that combinations of zinc benzoate and metal catalysts other than cadmium benzoate can be utilized to disproportionate a mixture of alkali metal benzoates at reaction temperatures near 400° C. The previously described procedure was used. The quantities of materials, reaction conditions, and results of each run are shown in Table VII.

TABLE VII

| Run[a,b] No. | ZnBz₂, ×10⁻⁴ mole | AgBz, ×10⁻⁴ mole | FeBz₃, ×10⁻⁴ mole | Temp., °C. | TPA Yield, mole % |
|---|---|---|---|---|---|
| 58 | 1.96 | — | — | 403 | 39 |
| 59 | — | 3.44 | — | 400 | trace |
| 60 | 1.96 | 1.94 | — | 404 | 52 |
| 61 | — | — | 3.4 | 405 | trace |
| 62 | 1.96 | — | 1.73 | 401 | 57 |

[a]Reaction time = 1 hour
[b]Alkali metal benzoates:
KBz = 1.98 g.
NaBz = 0.897 g.
CsBz = 0.124 g.

The results of these runs demonstrate that combinations of zinc benzoate and silver benzoate as well as combinations of zinc benzoate and ferric benzoate result in higher TPA yields in the disproportionation of mixtures of potassium benzoate, sodium benzoate, and cesium benzoate at about 400° C. than any of the individual catalysts.

EXAMPLE VIII (a) In this part in a run 63, not tabulated, zinc oxide in lieu of zinc benzoate was used.

In this run the reactor was charged with 1.44 g NaBz, 1.6 g KBz, 0.12 g CsBz, 0.12 g ZnO, and 6 g terphenyl. The reaction was carried out at 424° C. for 1 hour. Only a trace of TPA was detected in the reaction product. Thus, ZnO was not catalytic in run 63.

(b) In this part, in a run 64, not tabulated, a mixture of ZnO and benzoic acid was used. Thus a mixture containing 0.96 g NaBz, 2.133 g KBz, 0.12 g CsBz, 0.0316 g zinc oxide, 0.096 g benzoic acid, and 6.2 g terphenyl was oven dried at 150° for 2 hours and was charged to the reactor. The reaction was carried out at about 400° C. for 1 hour and a 60% yield of TPA was obtained.

These runs indicate that zinc oxide is not a suitable disproportionation catalyst under the conditions used in run 63, whereas a combination of zinc oxide and benzoic acid will result, as in run 64, is substantial disproportionation of a mixture of alkali metal benzoates.

EXAMPLE IX

A series of eight runs, 65 to 72, inclusive, see Table VIII, was carried out in which the alkali metals in the starting alkali metal benzoates were recovered at the conclusion of the reaction period as the benzoate and recycled to another disproportionation run. In each run, 24 g of the mixed alkali metal benzoates, 1 g of zinc benzoate, and 50 g of terphenyl were charged to a 300 ml stainless steel autoclave which was fitted with a thermocouple, pressure gauge, and a stirrer. The first run of this series, run 65, contained a NaBz/KBz/CsBz mole ratio of 12.3/25.3/1. The autoclave was sealed and purged three times with $CO_2$. The autoclave was pressured with $CO_2$ to about 500 psig (3.4 MPa) at about 70° C. and heated to a reaction temperature of 403°–406° C. The reaction was carried out with stirring and at the conclusion of the one hour reaction period the reaction mixture was cooled to room temperature by immersing the reactor in ice water. The reactor contents were mixed with 1500 ml toluene and the resulting mixture was heated and filtered to separate the insoluble solid alkali metal salts. The solid salts were washed with toluene, air dried for one hour, and weighed.

The crude alkali metal salts, i.e., terephthalate salts, were added to and dissolved in 200 ml distilled water and the insoluble material (carbonaceous material that contained zinc from the catalyst) was filtered, air dried, weighed and discarded. The filtrate was concentrated to about 60 ml and was mixed with 19 g benzoic acid in a 300 stainless steel autoclave. The mixture was heated at 135° C. with stirring for 30 minutes. The reactor was cooled by immersion in ice water and opened. The crude TPA product was filtered and washed with two-150 ml portions of distilled water. The solid was then washed with two-150 ml portions of boiling distilled water and air dried to yield TPA with a purity of about 98%.

The aqueous filtrate was extracted with 3-200 ml portions of ether to remove any benzoic acid and was evaporated to dryness. The solid alkali metal benzoates were used in the next run with 1 g of zinc benzoate, 50 g terphenyl, and makeup alkali metal benzoate mixture (in the same mole ratio as in the original charge) to bring the total alkali metal benzoate weight to 24 g. Elemental analyses of the recovered alkali metal benzoates showed that the weight % Na, K and Cs did not change significantly during the eight runs.

The results of each of these runs are shown in Table VIII. The % conversion was calculated by:

$$\text{Conversion (\%)} = \frac{\text{moles alkali metal benzoate consumed}}{\text{moles alkali metal benzoate charged}} \times 100$$

The % selectivities to TPA were calculated by:

$$\text{Selectivity to TPA (\%)} = \frac{\text{moles TPA recovered}}{\frac{1}{2} \times \text{moles alkali metal benzoate consumed}} \times 100$$

TABLE VIII

| Run[a] No. | Crude Alkali Metal Benzene Dicarboxylate Product | | Carbonaceous Material[b], wt. % | TPA Yield[c], mole % | Alkali Metal Benzoates Recovered g | Material Balance, % |
|---|---|---|---|---|---|---|
| | g | Conversion, mole % | Selectivity to TPA, mole % | | | |
| 65 | 20.3 | 76 | 63.5 | 3.4 | 44 | 21.9 | 90 |
| 66 | 20.3 | 82 | 85 | 2.2 | 58 | 22.3 | 93 |
| 67 | 20.2 | 77 | 83 | 2.5 | 55 | 22.5 | 94 |
| 68 | 20.7 | 82 | 92 | 2.7 | 64 | 23.2 | 97 |
| 69 | 20.1 | 74 | 78 | 3.8 | 48 | 22.2 | 93 |
| 70 | 20   | 81 | 87 | 3.9 | 60 | 22.3 | 93 |
| 71 | 19.8 | 80 | 84 | 3   | 56 | 22.1 | 92 |
| 72 | 20.2 | 79 | 79 | 3.6 | 53 | 22.8 | 95 |

[a]Alkali metal benzoates = 24 g. Zinc benzoate = 1 g. Terphenyl = 50 g. Reaction Temp. = 403–406° C. Reaction Pressure = 732–835 psig. Reaction time = 1 hour
[b]Weight % carbonaceous material calculated by:
$$\text{Weight \%} = \frac{\text{weight of water insoluble material}}{\text{weight of total crude product excluding the terphenyl dispersant}} \times 100$$
[c]Mole % TPA isolated based on the moles of alkali metal benzoates charged to the reactor These runs show that a significant amount of the alkali metals charged to the disproportionation reaction can be recovered from the reaction product by reaction with benzoic acid without significant change in the alkali metal content and the resulting alkali metal benzoates can be recycled to another disproportionation reaction.

Reasonable variation and modification are possible within the scope of the foregoing disclosure and claims to the invention the essence of which is that certain disclosed combinations of described carboxylates heated to reaction temperature in the presence of certain disclosed catalysts or combinations thereof made according to defined prescriptions have been found to give high yields and high reaction rates at lower than usual temperatures to produce terephthalates in an economically feasible and heat energy saving manner, without sacrificing high yields and high reaction rates.

I claim:

1. A process for converting alkali metal benzoates to alkali metal terepthalates which comprises heating to a reaction temperature in the range of from about 380° to about 430° C. at least two alkali metal benzoate salts selected from sodium, potassium and cesium benzoates, wherein each alkali metal benzoate is present in an amount equal to at least two weight percent of the total alkali metal benzoate present, in the presence of a catalyst selected from the benzoate salts of zinc, zinc and cadmium, zinc and silver, and zinc and iron, wherein when two salts are combined to form the catalyst each component of the catalyst will be present in amounts greater than about 10 mole percent of total catalyst, and wherein when the catalyst is zinc benzoate the alkali metal benzoates present are sodium, potassium, and cesium.

2. A process according to claim 1 wherein the alkali metal benzoates are sodium, potassium and cesium benzoate and the catalyst is composed of zinc and cadmium benzoates.

* * * * *